United States Patent [19]
Addor et al.

[11] 3,954,801
[45] May 4, 1976

[54] 2-IMINO-1,3-DITHIETANES

[75] Inventors: Roger Williams Addor, Pennington; Sidney Kantor, Trenton, both of N.J.

[73] Assignee: American Cyanamid Company, Stamford, Conn.

[22] Filed: June 27, 1974

[21] Appl. No.: 483,485

Related U.S. Application Data

[63] Continuation-in-part of Ser. No. 225,278, Feb. 10, 1972, abandoned.

[52] U.S. Cl. .............................. 260/327 M; 424/277
[51] Int. Cl.² .................................... C07D 339/06
[58] Field of Search .............................. 260/327 M

[56] References Cited
UNITED STATES PATENTS

| | | | |
|---|---|---|---|
| 3,442,907 | 5/1969 | Donche et al. | 260/327 |
| 3,484,455 | 12/1969 | Addor | 260/327 |
| 3,755,363 | 8/1973 | Timmons et al. | 260/327 |

*Primary Examiner*—Henry R. Jiles
*Assistant Examiner*—C. M. S. Jaisle
*Attorney, Agent, or Firm*—Robert P. Raymond

[57] ABSTRACT

This invention relates to novel aromatic 2-imino-1,3-dithietane compounds and compositions, as well as a method for the control of Ixodides, therewith. It further relates to methods for the preparation of said compounds and compositions.

5 Claims, No Drawings

2-IMINO-1,3-DITHIETANES

This application is a continuation-in-part of application Ser. No. 225,278, filed Feb. 10, 1972, now abandoned.

The present invention relates to certain novel aromatic 2-imino-1,3-dithietane compounds and compositions, together with methods for their use in control of Ixodides. It further relates to methods for the preparation of said compounds and compositions.

Among the depredations caused annually by Acarina, those attributable to the sub-order Ixodides are of considerable importance. In addition to causing weakness in their warm-blooded mammalian hosts, Ixodides serve as a very important vector of disease to said hosts. This results in a substantial annual economic loss and medical problem, especially with regard to domestic animals.

It has now been found that warm-blooded animals can be protected against attack by Ixodides by topically applying an effective amount of an aromatic 2-imino-1,3-dithietane compound having the Formula I below to said hosts:

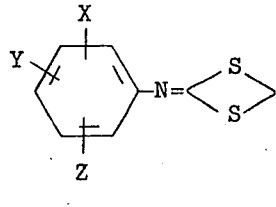

wherein X, Y and Z each represent a member selected from the group consisting of hydrogen, halogen, hydroxy, R(M)n, phenoxy, monohalophenoxy, nitro, trihalomethyl, cyano, isothiocyano, carbloweralkoxy $C_1-C_8$, diloweralkylamino, monoloweralkylamino, 1,3-dithietanylideneamino; R is a member selected from alkyl $C_1-C_8$, cycloalkyl $C_5-C_7$, alkenyl $C_3-C_8$, alkynyl $C_3-C_8$; M is sulfur or oxygen; n is an integer of 0 or 1; and when two of X, Y and Z are taken together on adjacent carbons they may form a benzo group.

The above substituents are illustrated as follows. Suitable halogen groups include, fluoro, chloro, bromo and iodo groups; suitable monohalophenoxy groups include, fluorophenoxy, chlorophenoxy, bromophenoxy, and iodophenoxy groups substituted in the o, m or p positions; suitable trihalomethyl groups include trifluoromethyl, trichloromethyl and tribromomethyl groups; suitable carbloweralkoxy groups include carbomethoxy, carbethoxy, carbobutoxy, carbopentoxy, carbohexoxy, carboheptoxy and carboctoxy groups; suitable mono and diloweralkylamino groups include those having $C_1$ to $C_4$ N-substituents; suitable alkenyl and alkynyl groups include both terminally unsaturated groups and groups having unsaturation within the chain.

Preferred groups within the definition of R(M)n include alkoxy, $C_1-C_4$, alkyl, $C_1-C_4$, and alkylthio, $C_1-C_4$.

Control of the Ixodide population is effected by means of the chemosterilant activity which the Formula I compounds exert upon the adult females. This method of control is useful against Argasidae or Ixodidae ticks including, for example, those of the following types: Boophilus, Amblyomma, Anocentor, Dermacentor, Ixodes, Haemaphysalis, Hyalomma, Rhipicentor, Margaropus, Rhipicephalus, Argas, Otobius and Ornithodoros.

The novel aromatic 2-imino-1,3-dithietanes of the present invention are within those of Formula I above. The novel compounds are those set forth as Formula II below:

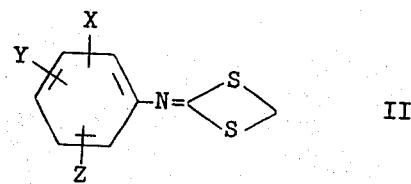

wherein X, Y and Z each represent a member selected from the group consisting of hydrogen, halogen, hydroxy, R(M)n, phenoxy, monohalophenoxy, nitro, trihalomethyl, cyano, isothiocyano, carbloweralkoxy $C_1-C_8$, diloweralkylamino, monoloweralkylamino, 1,3-dithietanylideneamino; R is a member selected from alkyl $C_1-C_8$, cycloalkyl $C_5-C_7$, alkenyl $C_3-C_8$, alkenyl $C_3-C_8$; M is sulfur or oxygen; n is an integer of 0 or 1; and when two of X, Y and Z are taken together or adjacent carbons they may form a benzo group; with the proviso that X, Y and Z cannot each be hydrogen and that when one of X, Y and Z is halogen or loweralkyl, at least one of the remaining substituents must be other than hydrogen.

For use as chemosterilants in the practice of the present invention compounds having ortho substitution are generally preferred. The diethietanes of the following group, known as group III compounds, are especially preferred for this purpose: 2-p-chloro-o-methylphenylimino-1,3-dithietane, 2-p-bromo-o-methylphenylimino-1,3-dithietane, 2-o-methylphenylimino-1,3-dithietane, 2-(2,5-dimethylphenylimino)-1,3-dithietane, 2-(2,4,5-trimethylphenylimino)-1,3-dithietane, 2-m-chloro-o-methylphenylimino-1,3-dithietane, 2-o,p-dimethylphenylimino-1,3-dithietane, 2-o,p-dichlorophenylimino-1,3-dithietane, 2-o,m-dichlorophenylimino-1,3-dithietane, 2-o-methoxyphenylimino-1,3-dithietane.

The diethietanes of Formulas I and II may be conveniently prepared by reacting the appropriately substituted phenyl dithiocarbamate salt with a methylene source in the presence of a base and an organic solvent. Thereby, the desired 2-phenylimino-1,3-dithietane is produced by the ring closing reaction which results.

The process for preparing the Formula II compounds of the present invention is schematically set forth as follows:

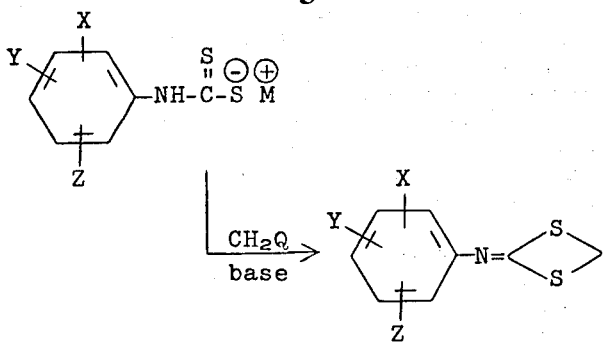

where $CH_2Q$ is a methylene source; $\overset{\oplus}{M}$ is a cation; and, X, Y and Z are as defined in Formula II above.

Suitable bases for use in the ring closure reaction include, for example, strong and weak bases, such as alkali metal hydroxides, carbonates, and bicarbonates, as well as tertiary amines, such as triethylamine. Methylene bromide and iodide are preferably employed as the methylene source in the ring closing reaction. Among the suitable organic solvents may be mentioned dimethylformamide, methanol and 1,2-dimethoxyethane.

The carbamate salts may be conveniently prepared by reacting the appropriate aniline, which are well known in the chemical literature, with carbon disulfide in the presence of a base. Alkali metal hydroxides, ammonia or tertiary amines may be conveniently employed as the base to produce the corresponding alkali metal or ammonium salts. An alternative route to the carbamate intermediates is to react the appropriate aryl isothiocyanate with an alkali metal hydrosulfide in a suitable solvent. The resulting alkali metal carbamate is then readily convertible to the desired dithietane by ring closure as described above.

In carrying out the ring closure reaction, the quantities of ingredients is not critical; however, since the carbamate and methylene source are combined in equimolar quantities in the formation of the dithietane, it is preferred to employ substantially equimolar quantities of the reactants or a small molar excess of the methylene compound. Reaction is initiated by merely admixing the reactants in the presence of a base and solvent. The reaction vessel is preferably cooled to maintain the reaction mixture at a temperature in the range of from about 0°C. to about 50°C. and preferably from about 12°C. to about 20°C. Work-up of the reaction product can be achieved in a conventional manner. The formation of the acid salt, such as the hydrochloride, provides a convenient means for the purification of the dithietane produced. Precipitation of the salt is effected by merely adding hydrochloric acid to a solution of the dithietane in a solvent such as ethylene chloride. The solid product is collected by filtration, washed and dried in a conventional manner. It may be conveniently reconverted to the dithietane by treatment with a base, such as aqueous ammonium hydroxide.

As previously mentioned, group III compounds are preferred in the present method for the control of Ixodides. These compounds have the common characteristic of an ortho substituent. The preferred process for preparing dithietanes accordingly involves the ring closure reaction between methylene bromide and a dithiocarbamate corresponding to one of the following anilines, conducted in an organic solvent with a base.

The anilines are: p-chloro-o-methylaniline, p-bromo-o-methylaniline, o-methylaniline, 2,5-dimethylaniline, 2,4,5-trimethylaniline, m-chloro-o-methylaniline, o,p-dimethylaniline, o,p-dichloroaniline, o,m-dichloroaniline and o-methoxyaniline.

Control of Ixodide is achieved by applying the dithietanes of Formula I to the adult females. Application can be made directly or indirectly. It is generally effected by topically applying the active ingredients, namely, the dithietanes of Formula I onto the host to be protected or the habitat of the Ixodide.

Application is generally facilitated by employing a composition containing an effective amount of the dithietane in combination with an inert agricultural adjuvant. One or more of the conventional solid and liquid carriers, diluents and formulation aids may be employed as the adjuvant. Furthermore, in addition to employing a single dithietane as the active ingredient, several of the Formula I dithietanes or one or more of the dithietanes in combination with a conventional pesticide may be employed.

The dithietanes may be conveniently formulated as dusts, dust concentrates, wettable powders, emulsifiable concentrates and the like. Application thereof is made in conventional manners, such as, by spraying, dusting, dipping in baths and the like.

Solid formulations, such as dusts or dust concentrates, can be prepared by grinding together the inert solid diluent such as attapulgite, kaolin, walnut shell flour, diatomaceous earth, ground corn cob grits, or ground cocoanut shell, and the active ingredient, where such active ingredient is in solid form. Where the active ingredient is liquid, it may be sprayed on the carrier and thoroughly mixed therewith or it may be dissolved in a solvent such as acetone, lower akanol, xylene, toluene or the like, and then sprayed as a dilute solution on the solid carrier. Dusts usually contain from about 1% to 15% by weight of active ingredient, whereas concentrates may contain from about 16% to about 85% by weight of the active material.

Wettable powders are prepared in the same fashion as dust concentrates excepting that about 5% to 10% by weight of a surfactant is also added. The wettable powder is then generally dispersed in water or other suitable diluent for application as a dilute liquid spray onto the Ixodide, host or locus where control is desired or as a bath for dipping animal hosts.

The Formula I dithietanes may also be prepared as emulsifiable concentrates by dissolving or dispersing about 10% to 75% by weight of the active compound in a suitable solvent or carrier such as a petroleum distillate having a minimum aromatic content of 85% and admixing therewith about 10% by weight of an emulsifier such as polyoxyethylene derivatives and blends with alkyl aryl sulfonates. These concentrates are also generally dispersed in water or other suitable solvent for application by spraying or by dipping the animal host.

Application of the dithietanes at rates in the range of from about 250 to 2500 ppm. is generally preferred.

In addition, certain of the compounds of Formula I are useful for improving feed efficiency and enhancing the growth rate of poultry, fur-bearing and farm animals by orally or parenterally administering to said animals a growth-promoting amount of said compounds as set forth in copending application Ser. No. 409,838, filed Oct. 26, 1973, now abandoned, having a common assignee.

In this regard, the feed efficiency in the raising of poultry such as chickens and turkeys, fur-bearing animals (i.e., animals raised for their pelts such as mink, rabbit and sable), and farm animals (i.e., livestock such as sheep, cattle, swine and goats), can be improved by orally or parenterally administering to the host an effective amount of a 2-arylimino-1,3-dithietane, and preferably an orthosubstituted 2-arylimino-1,3-dithietane. Administration of said dithietane measurably enhances the growth rate of said animal.

The growth rate of poultry, fur-bearing animals and farm animals is measurably improved when a 2-arylimino-1,3-dithietane is administered to the above-said host, in or with the feed in an amount equivalent to between 0.0001% to 0.05%, and preferably 0.001% to 0.02% by weight of the feed.

In practice, the active material will generally be formulated as a premix and/or an animal feed supplement which is admixed with a nutritionally balanced feed or added to said feed as a top dressing, or the like.

Premixes may be prepared by blending about 80% to 99% by weight of rice flower, ground rice hulls, ground corn, or the like, with about 1% to 20% by weight of the 2-arylimino-1,3-dithietane. From about 0.2% to 2%, and preferably about 0.5% to 1.0% by weight of the premix, is then blended with other edible substances including vitamins, minerals and feedstuffs to form a feed supplement or complete diet.

A typical cattle supplement is described below.

| Beef Cattle Supplement | Feed Rate | |
|---|---|---|
| | 2 lbs/Head/Day | 1 lb/Head/Day |
| Dehydrated Alfalfa Meal (17%) | 13.0% | 26.5% |
| Cotton Seed Meal (41%) | 13.5% | 27.0% |
| Limestone (33%) | 11.0% | 22.0% |
| Urea (2.81%) | 6.0% | 12.0% |
| Dried Molasses | 2.5% | 5.0% |
| Salt, Iodized | 2.5% | 5.0% |
| Vitamin-Mineral Premix[1] | 1.0% | 2.0% |
| Drug Premix[2] | 0.5% | 0.5% |
| Ground Corn | 50.0% | — |

[1] Vitamin-Mineral Premix (per 1000 lbs of supplement)

| | | |
|---|---|---|
| Vitamin A (30,000 I.U./g) | 833 g | 1666 g |
| Cobalt Sulfate ($CoSO_4 \cdot 7H_2O$) | 2 g | 4 g |
| Copper Sulfate ($CuSO_4 \cdot 5H_2O$) | 78 g | 156 g |
| Manganese Oxide (MnO) | 32 g | 64 g |
| Zinc Oxide (ZnO) | 62 g | 124 g |
| Elemental Sulfur | 2000 g | 4000 g |
| Dehydrated Alfalfa Meal | 1533 g | 3066 g |
| | 4540 g | 9080 g |

[2] Drug Premix (per 1000 lbs of supplement)

| 2-Arylimino-1,3-dithietane Level of Drug per Head/Day (mg) | Amount in Premix | | Amount in Premix | |
|---|---|---|---|---|
| | Drug (g) | Ground Corn (g) | Drug (g) | Ground Corn (g) |
| 400 | 200 | 2070 | 400 | 1870 |
| 200 | 100 | 2170 | 200 | 2070 |
| 100 | 50 | 2220 | 100 | 2170 |
| 50 | 25 | 2245 | 50 | 2220 |
| 0 | 0 | 2270 | 0 | 2270 |

The growth rate of animals is also improved when the dithietane is administered as a subcutaneous implant under the skin of the animal. Implants are generally in the form of a paste or pellet which permits the active compound to be released into the bloodstream of each animal over an extended period of time; as for example, from several weeks to several months.

Whether the implant is in the form of a paste or a pellet is simply a matter of choice. The important factor is the amount of drug to be administered. Formulations and intervals between administration should be varied to give about 0.001 mg. to 0.2 mg. of the dithietane per kg. of animal body weight per day, and preferably from 0.01 mg. to 0.10 mg. per kg. of animal body weight per day will enhance the growth rate of animals and improve feed efficiency.

Pellet-type implants which can be used in accordance with this invention may be prepared by admixing from about 50% to 95% by weight of the 2-arylimino-1,3-dithietane with from about 50% to 5% by weight of a pharmaceutically acceptable carrier such as Castor wax (i.e., glyceryl 12-hydroxy stearate), white wax, beeswax, starch, or a high molecular weight (4000) polyethylene glycol, or mixtures thereof, alone or in combination with a small amount of a lubricant such as zinc or magnesium stearate. A small amount of polyvinylpyrrolidone and dibutylphthalate may also be incorporated in the above-said formulations.

Typical formulations which can be used are as follows:

| | | Preferred |
|---|---|---|
| (A) | 2-Arylimino-1,3-dithietane (50% to 95%) | 50.0% |
| | Lubricant (i.e. magnesium stearate) | 0.5% |
| | Castor wax - QS | |
| (B) | 2-Arylimino-1,3-dithietane | 60.0% |
| | Polyethylene glycol 4000 | 10.0% |
| | Beeswax - QS | |
| (C) | 2-Arylimino-1,3-dithietane | 30.0 mg |
| | Beeswax | 1.0 mg |
| | Magnesium stearate | 1.5 mg |
| | Dibutylphthalate | 1.0 mg |
| | Polyvinylpyrrolidone (10% Solution) - QS | |

Paste implants can be prepared using the same percentages of drug as stated above but employing a mixture of high molecular weight (4000) and low molecular weight (400) polyethylene glycol alone or in combination with castor wax or beeswax and/or polyvinylpyrrolidone. A typical paste can be prepared as follows:

| | | Preferred |
|---|---|---|
| (A) | 2-Arylimino-1,3-dithietane (100 mg to 600 mg) | 200 mg |
| | Polyethylene glycol 4000 (30% to 50%) | 40% |
| | Polyethylene glycol 400 - QS | |

Implants may vary in size and weight, but usually range between 5 mg. and 100 mg. per implant with multiple implants being used to supply the necessary drug to larger animals.

The preparation of the dithietanes employed in the present invention and their chemosterilant effect in Ixodides and use as growth promoters is demonstrated in the examples which follow, which are not to be taken as being limitative of the present invention. In each case, parts and percentages are by weight unless otherwise indicated.

EXAMPLE 1

Preparation of 2-(p-Tolylimino)-1,3-dithietane

To an ice-cooled mixture of 3,330 ml. of aqueous ammonium hydroxide (28%) and 6,640 ml. of water in a suitable reaction vessel is added a mixture of 3,570 grams of p-toluidine and 2,350 grams of carbon disulfide in 3,330 ml. of i-propyl alcohol over about a 1.5 hour period. By cooling, the mixture is maintained below about 10°C. After an additional 1.0 hour to 1.5 hours, the solids are collected by filtration, washed with methyl ethyl ketone, and air-dried overnight. The ammonium p-tolyldithiocarbamate, melting point 93°C. to 95°C. (decomposition) is recovered in the amount of 4,930 grams.

In a suitable reaction vessel is mixed 6,090 grams of methylene bromide, 1,955 grams of sodium bicarbonate and 13.2 liters of dimethylformamide. The mixture is cooled to 12°C. and maintained between 12°C. and 20°C. while adding powdered ammonium p-tolyldithiocarbamate in small portions over about a 2-hour period. After stirring for an additional 4 hours at room temperature, the mixture is poured into a separatory funnel and diluted with an equal volume of water. The lower oily phase is separated and the upper aqueous DMF phase is extracted three times with 3.5 liter portions of ethylene chloride. The combined organic phase is washed with water and filtered. In a suitable vessel, the washed ethylene chloride mixture is diluted with an additional 36 liters of ethylene chloride, cooled to 10°C. to 15°C., and well stirred while adding 3,690 ml. of 37% aqueous solution of hydrochloric acid. After the mixture comes to room temperature, the solids are collected by filtration and washed with ethylene chloride and then methyl ethyl ketone. The air-dried hydrochloride salt of 2-p-tolylimino-1,3-dithietane, amounting to 3,432 grams, is finely pulverized and mixed with 14.5 liters of water. The mixture is cooled and about 2800 ml. of ammonium hydroxide is added over about 30 minutes to give a final acidity of pH 8. The solids are collected by filtration, washed with water, and air-dried to give 2,566 grams of 2-p-tolylimino-1,3-dithietane, melting point 54.5°C. to 55.0°C. The infrared spectrum shows C=N absorption at 1640 cm.$^{-1}$.

EXAMPLE 2

Preparation of
2-(4-Chloro-2-methylphenyl)imino-1,3-dithietane

To a well-stirred mixture of 2,615 grams of 4-chloro-2-methylaniline in 9200 ml. of dimethylformamide in a water-cooled flask is added 739 grams of porous sodium hydroxide beads followed by 1,406 grams of carbon disulfide. When solution of the sodium hydroxide is nearly complete (1 to 2 hours with temperature kept below 50°C. by cooling), the mixture is added slowly to 6,440 grams of methylene bromide and 1,553 grams of sodium bicarbonate well stirred in 9,300 ml. of dimethylformamide. The addition time is about one hour with the reaction temperature kept below ca. 50°C. by external cooling. After an additional 2 hours at room temperature, the reaction mixture is poured into an equal volume of water and the organic material is partitioned into ethylene chloride. The ethylene chloride mixture is washed with water and with 5% hydrochloric acid and filtered free of some insoluble material. The ethylene chloride mixture is cooled to between 10°C. to 15°C. and 2,310 ml. of a 37% aqueous solution of hydrochloric acid is added slowly with stirring. The resulting solids are collected by filtration, washed with ethylene chloride and methyl ethyl ketone, and air-dried to give 1,709 grams of the hydrochloride salt. The pulverized salt is stirred in water and 428 grams of 28% aqueous ammonia are added. The resulting oil, after recovery by extraction with ethylene chloride and solvent removal under vacuum, amounts to 1,333 grams. The resulting crystalline dithietane melts at from 43°C. to 46°C. The infrared spectrum shows strong C=N absorption at 1630 cm.$^{-1}$.

EXAMPLE 3

Preparation of 2-(m-Nitrophenylimino)-1,3-dithietane

A mixture of 75.0 grams of potassium t-butylate in 500 ml. of t-butyl alcohol is saturated with hydrogen sulfide. With the temperature kept below 35°C. by cooling, a mixture of 120.0 grams of m-nitrophenyl isothiocyanate in 500 ml. of ether is added to the potassium hydrosulfide solution in three portions. After the mixture is stirred an additional 2 hours, the solids are collected by filtration, washed with ether, and dried under vacuum to give 162 grams of potassium m-nitrophenyldithiocarbamate. This salt is added portionwise over about 15 minutes to a stirred ice-cooled mixture of 174 grams of methylene bromide and 65 grams of triethylamine in 600 ml. of dimethylformamide with the reaction temperature at 25°C. to 30°C. After another 5 hours of stirring at room temperature, the mixture is poured into 3.5 liters of ice-water precipitating a light yellow solid. The solids, after drying, are taken up in benzene (ca. 2 liters), filtered free of some insoluble material, and the benzene mixture is saturated with dry hydrogen chloride. The precipitated solids are collected by filtration, washed with benzene, and then stirred vigorously with a water-benzene mixture at 60°C. to 70°C. The benzene layer is separated, washed with water and sodium bicarbonate solution, dried, and concentrated in vacuo to give 102 grams of crude product. The solids are dissolved in 800 ml. of ethanol. The mixture is filtered and diluted with 1200 ml. of ether. Then the mixture is cooled to −35°C. The resulting light yellow solids are collected and vacuum dried to give 84.0 grams of product, melting point 96.0°C. to 97.0°C.

EXAMPLES 4 THROUGH 66

Following the procedure of Example 2 above and substituting the appropriate aniline for 4-chloro-2-methylaniline in said procedure yields the compounds set forth in Table I below.

TABLE I

Aromatic 2-Imino-1,3-Dithietanes

| Ex. No. | X | Y | Z | Melting Point °C. |
|---|---|---|---|---|
| 4 | 4-Cl— | H | H | 86.8–88 |
| 5 | 4-CH$_3$— | H | H | 168–170[a] |
| 6 | 4-C$_2$H$_5$— | H | H | oil |
| 7 | 4-n-C$_4$H$_9$— | H | H | oil |
| 8 | 4-(C$_6$H$_5$)O— | H | H | 67.5–68.5 |
| 9 | 4-CH$_3$—O—C(O)— | H | H | 79–80 |
| 10 | 4-(CH$_3$)$_2$—N— | H | H | 96–98 |
| 11 | 4-S=C=N— | H | H | 121–122 |
| 12 | 4-(4-Cl-C$_6$H$_4$)O— | H | H | 58.5–59 |
| 13 | 4-(dithietane-2-ylidene)N— | H | H | 220–223 |
| 14 | 3-CH$_3$— | H | H | 28.5–29.5 |
| 15 | 3-CF$_3$— | H | H | oil |
| 16 | 3-C$_2$H$_5$O— | H | H | oil |
| 17 | 3-Cl— | H | H | 76–77 |
| 18 | 3-Br— | H | H | 67.5–69.5 |
| 19 | 3-(C$_6$H$_5$)O— | H | H | oil |
| 20 | 3-CH$_3$—S— | H | H | oil |
| 21 | 3-C$_2$H$_5$COO— | H | H | 62.5–63.5 |
| 22 | 2-CH$_3$— | H | H | 34–35 |
| 23 | 2-Cl— | 3-Cl— | H | 77–79 |
| 24 | 2-CH$_3$— | 3-Cl— | H | 80–81.5 |
| 25 | 2-CH$_3$— | 4-CH$_3$— | H | oil |
| 26 | 2-Cl— | 4-Cl— | H | 95–97 |
| 27 | 2-CH$_3$— | 4-Br— | H | oil |
| 28 | 2-Br— | 4-CH$_3$— | H | 63–65 |
| 29 | 2-Cl— | 4-NO$_2$— | H | 103–104 |
| 30 | 2-CH$_3$— | 5-C$_3$H$_7$-i- | H | oil |
| 31 | 2-Cl— | 5-Cl— | H | 98–99 |
| 32 | 2-C$_2$H$_5$— | 6-C$_2$H$_5$— | H | 56–57 |
| 33 | 3-CH$_3$— | 4-CH$_3$— | H | oil |
| 34 | 3-Cl— | 4-CH$_3$— | H | 80–80.5 |
| 35 | 3-Cl— | 4-Cl— | H | 100–101.5 |
| 36 | 3-CF$_3$— | 4-Cl— | H | oil |
| 37 | 3-Cl— | 5-Cl— | H | 106–108 |
| 38 | 2-Cl— | 4-Cl— | 5-Cl— | 96.5–98.5 |
| 39 | 2-CH$_3$— | 4-CH$_3$— | 5-CH$_3$— | 41–42 |
| 40 | 3-Cl— | 4-CH$_3$O— | 6-CH$_3$O— | 104.5–106 |
| 41 | 2-Cl— | 4-C$_8$H$_{17}$— | H | — |
| 42 | H | H | H | — |
| 43 | 4-OH— | H | H | 162–163 |
| 44 | 4-CH$_3$S— | H | H | 76–77.5 |
| 45 | 4-F— | H | H | 59–60 |
| 46 | 4-I— | H | H | 139.5–141 |
| 47 | 4-CH$_3$O— | H | H | 37.5–38.5 |
| 48 | 4-CN— | H | H | 78.5–79.5 |
| 49 | 4-NO$_2$— | H | H | 135–137 |
| 50 | 3-CN— | H | H | 114–115 |
| 51 | 2-Cl— | H | H | 42.5–44 |
| 52 | 2-CH$_3$O— | H | H | 112–114 |
| 53 | 2-Cl— | 4-CH$_3$— | H | 67.5–70.5 |
| 54 | 2-CH$_3$— | 4-NO$_2$— | H | 128.5–130.5 |
| 55 | 2-CH$_3$— | 5-CH$_3$— | H | 33–34 |

TABLE I-continued
Aromatic 2-Imino-1,3-Dithietanes

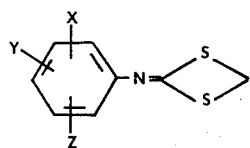

| Ex. No. | X | Y | Z | Melting Point °C. |
|---|---|---|---|---|
| 56 | 3-CH₃— | 4-Br— | H | 71–73 |
| 57 | 3-CH₃O— | 4-CH₃O— | H | 82.5–83.5 |
| 58 | 2,3-benzo— | | H | 103–105 |
| 59 | 2-CH₂=CHCH₂— | H | H | — |
| 60 | 4-HC≡CCH₂O— | H | H | — |
| 61 | 3-C₅H₉— | H | H | — |
| 62 | 4-C₆H₁₁— | H | H | — |
| 63 | 3-CH₂=CCH₃CH₂S— | H | H | — |
| 64 | 4-C₇H₁₃O— | H | H | — |
| 65 | 4-CH₂=CHCH₂— | Cl— | H | — |
| 66 | 3-C₇H₁₅O— | H | H | — |

"as the hydrochloride

EXAMPLE 67

Efficacy of the dithietanes as chemosterilants for Ixodides is demonstrated in the following tests wherein adult female *Boophilus microplus* ticks which have dropped from cattle are collected and used for testing.

The compound to be tested is dissolved in a 35% acetone/65% water mixture in sufficient amount to provide from about 500 ppm. to 2000 ppm. of compound in the test solution. Ten ticks per treatment are used and they are immersed in test solution for 3 to 5 minutes. Thereafter, they are removed and placed in cages and held at room temperature for 3 days. Counts of ticks laying eggs are then made and recorded. For these tests, non-resistant ticks as well as ethion-resistant and dioxathion-resistant ticks are used since the latter two are among the most difficult of their kind to control. Results of these tests are given in Table II below. The rating system used is as follows:

Rating System

+ = >50% did not lay eggs when treated at 2000 ppm.
++ = >50% did not lay eggs when treated at 1000 ppm.
+++ = >50% did not lay eggs when treated at 500 ppm.
O = more than 50% layed eggs when treated at 2000 ppm.
M = ethion-resistant ticks
D = dioxathion-resistant ticks
S = non-resistant

TABLE II

| Compound Example Number | Ticks | | |
|---|---|---|---|
| | M | D | S |
| 1 | + | + | ++ |
| 7 | 0 | + | ++ |
| 8 | + | 0 | + |
| 9 | 0 | 0 | + |
| 16 | 0 | 0 | + |
| 22 | +++ | +++ | +++ |
| 51 | 0 | + | +++ |
| 52 | + | ++ | +++ |
| 23 | +++ | ++ | +++ |
| 24 | +++ | +++ | +++ |
| 2 | +++ | +++ | +++ |
| 25 | +++ | +++ | +++ |
| 26 | ++ | +++ | +++ |
| 27 | +++ | ++ | +++ |
| 28 | 0 | + | +++ |
| 53 | 0 | ++ | +++ |
| 29 | + | 0 | 0 |
| 30 | + | + | + |
| 55 | +++ | +++ | +++ |
| 32 | + | ++ | ++ |
| 33 | 0 | + | ++ |
| 34 | ++ | 0 | ++ |
| 56 | ++ | + | + |
| 39 | +++ | +++ | +++ |
| 58 | ++ | ++ | ++ |

EXAMPLE 68

The test of Example 67 was repeated using various dithietanes, applied at various concentrations. The results of these tests are set forth in Table III below.

TABLE III

| Compound Example Number | ppm. Compound | Number Ticks Treated | Number Ticks Producing Eggs | Number Sterile Egg Batches | % Sterile Egg Batches |
|---|---|---|---|---|---|
| 1 | 2000 | 30 | 12 | 6 | 50 |
| | 1000 | 29 | 22 | 4 | 18 |
| | 500 | 29 | 26 | 4 | 15 |
| | 0 | 60 | 53 | 4 | 7.5 |
| 7 | 2000 | 30 | 24 | 13 | 54 |
| | 1000 | 30 | 27 | 4 | 15 |
| | 0 | 60 | 53 | 4 | 7.5 |
| 8 | 2000 | 30 | 27 | 9 | 33 |
| | 1000 | 30 | 25 | 3 | 12 |
| | 500 | 30 | 27 | 11 | 41 |
| | 0 | 60 | 51 | 9 | 17.5 |
| 9 | 2000 | 29 | 27 | 8 | 30 |
| | 1000 | 30 | 28 | 6 | 21 |
| | 500 | 30 | 27 | 3 | 11 |
| | 0 | 60 | 53 | 4 | 7.5 |
| 16 | 2000 | 30 | 26 | 8 | 33 |
| | 1000 | 30 | 27 | 7 | 39 |
| | 500 | 30 | 24 | 5 | 21 |
| | 0 | 60 | 51 | 9 | 17.5 |
| 22 | 500 | 29 | 10 | 7 | 70 |
| | 0 | 60 | 53 | 4 | 7.5 |
| 52 | 2000 | 29 | 9 | 5 | 56 |
| | 1000 | 30 | 19 | 9 | 47 |
| | 500 | 30 | 24 | 10 | 42 |
| | 0 | 58 | 53 | 0 | 0 |
| 23 | 1000 | 30 | 13 | 4 | 31 |
| | 500 | 30 | 20 | 6 | 30 |
| | 0 | 60 | 53 | 4 | 7.5 |
| 24 | 1000 | 30 | 9 | 8 | 89 |
| | 500 | 30 | 17 | 11 | 65 |
| | 0 | 60 | 60 | 0 | 0 |

TABLE III-continued

| Compound Example Number | ppm. Compound | Number Ticks Treated | Number Ticks Producing Eggs | Number Sterile Egg Batches | % Sterile Egg Batches |
|---|---|---|---|---|---|
| 2 | 2000 | 30 | 8 | 7 | 88 |
|   | 1000 | 30 | 10 | 10 | 100 |
|   | 500 | 30 | 7 | 5 | 72 |
|   | 0 | 60 | 60 | 0 | 0 |
| 25 | 2000 | 30 | 2 | 2 | 100 |
|   | 1000 | 30 | 9 | 6 | 67 |
|   | 500 | 29 | 8 | 2 | 25 |
|   | 0 | 60 | 51 | 9 | 18 |
| 26 | 2000 | 30 | 5 | 5 | 100 |
|   | 1000 | 30 | 10 | 5 | 50 |
|   | 500 | 30 | 14 | 2 | 14 |
|   | 0 | 60 | 58 | 1 | 1.7 |
| 27 | 2000 | 30 | 7 | 7 | 100 |
|   | 1000 | 30 | 8 | 7 | 88 |
|   | 500 | 30 | 13 | 8 | 62 |
|   | 0 | 60 | 56 | 1 | 1.8 |
| 28 | 2000 | 30 | 19 | 5 | 26 |
|   | 1000 | 30 | 16 | 2 | 12 |
|   | 500 | 30 | 23 | 6 | 26 |
|   | 0 | 60 | 56 | 1 | 1.8 |
| 53 | 2000 | 30 | 16 | 4 | 25 |
|   | 1000 | 30 | 20 | 5 | 25 |
|   | 500 | 30 | 24 | 5 | 21 |
|   | 0 | 60 | 56 | 1 | 1.8 |
| 30 | 2000 | 30 | 19 | 10 | 53 |
|   | 1000 | 30 | 27 | 2 | 7 |
|   | 0 | 60 | 53 | 4 | 7.5 |
| 55 | 1000 | 30 | 13 | 13 | 100 |
|   | 500 | 30 | 13 | 9 | 69 |
|   | 0 | 60 | 56 | 1 | 1.8 |
| 32 | 1000 | 29 | 14 | 3 | 21 |
|   | 500 | 30 | 28 | 3 | 11 |
|   | 0 | 60 | 53 | 4 | 7.5 |
| 33 | 2000 | 30 | 13 | 3 | 23 |
|   | 1000 | 30 | 25 | 7 | 28 |
|   | 0 | 60 | 53 | 4 | 7.5 |
| 34 | 2000 | 30 | 20 | 8 | 40 |
|   | 1000 | 30 | 22 | 4 | 18 |
|   | 500 | 30 | 25 | 3 | 12 |
|   | 0 | 60 | 51 | 9 | 17.5 |
| 56 | 2000 | 30 | 19 | 5 | 26 |
|   | 0 | 60 | 53 | 6 | 11 |
| 39 | 2000 | 30 | 6 | 6 | 100 |
|   | 1000 | 30 | 7 | 6 | 86 |
|   | 500 | 30 | 16 | 7 | 23 |
|   | 0 | 60 | 56 | 1 | 1.8 |

EXAMPLE 69

Mouse Growth Regulant Evaluation

Six-week-old female Carworth CF-1 mice, averaging 18 to 21 grams in weight, are placed 10 to a cage and fed Purina Laboratory Chow ad libitum for 13 days. At the end of this feeding period, the mice are weighed and fed diets containing the experimental compounds for a 12-day period. At the end of the test feeding period, the mice are weighed and the gain for the period recorded. This gain is then compared to the gain of control animals. Experimental compounds are fed at 200 ppm in the diet. The diet used is reported below and data obtained are reported in Table IV, where growth enhancement is reported as percent increase over controls. Control animals received the same diet as test animals but without test compound added.

In each instance, animals receiving test compound were noticeably larger than control animals and had better looking pelts than the control animals.

| DIET | |
|---|---|
| Crude protein not less than | 23.0% |
| Crude fat not less than | 4.5% |
| Crude fiber not more than | 6.0% |
| Ash not more than | 9.0% |

INGREDIENTS

Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewers' dried yeast, thiamin, niacin, vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide.

TABLE IV

Growth Enhancement of Mice Reported as Percent Increase in Weight Gain Over Untreated Controls

| X | Y | Z | % Increase Over Controls |
|---|---|---|---|
| 4-Cl | 2-$CH_3$ | H | 31.0 |
| 2-Br | 4-$CH_3$ | H | 44.7 |
| 2-Cl | 4-$CH_3$ | H | 35.8 |

EXAMPLE 70

Growth Enhancement and Feed Efficiency Evaluations in Sheep

To determine the effect of feeding a 2-arylimino-1,3-dithietane compound to sheep, wether lambs are randomly allotted to pens in groups of six. The sheep are weighed and permitted food and water ad libitum. The feed is weighed daily, and uneaten feed from the previous day collected and weighed. Lambs receiving unmedicated diet are used as controls, while treated lambs receive the same diet but with 20 ppm or 60 ppm (parts per million) of test drug added. At the end of the six-week treatment period, the lambs are again weighed, and total feed consumed is calculated.

Six-week weight gains are presented in Table V and kg. feed per kg. gain in Table VI. From these data it can be seen that lambs fed at 20 ppm. and 60 ppm. for 6 weeks improved gain by 15.3% and 11.1%, respectively. Feed utilization was improved by 10.0% and 9.8% for the 20 ppm. and 60 ppm. levels.

| LAMB DIET | |
|---|---|
|  | % |
| Ground Corn Cob | 15.0 |
| Ground Yellow Corn | 48.0 |
| Soybean Oil Meal (49%) | 10.0 |
| Dehydrated Alfalfa Meal | 15.0 |
| Molasses | 10.0 |

-continued

| LAMB DIET | |
|---|---|
| Iodized Salt | 0.5 |
| Dicalcium Phosphate | 1.0 |
| Premix | 0.5 |
| | 100.0 |

| Premix for One Ton | |
|---|---|
| Tra-Min No. 3[1] | 454 grams |
| Vitamin A (30,000 μ/g) | 133 |
| Vitamin $D_3$ (200,000 μ/g) | 5 |
| Corn Oil | 100 |
| Ground Corn | 3848 |
| | 4520 |

| [1]Tra-Min No. 3: | | |
|---|---|---|
| | Calcium | 21.00% |
| | Manganese | 12.50% |
| | Iron | 6.00% |
| | Zinc | 5.00% |
| | Copper | 0.65% |
| | Iodine | 0.35% |
| | Cobalt | 0.25% |

TABLE V

| Treatment | Level (ppm) | Six-Week Feed Efficiency (kg Feed/kg Gain) Replication | | | | Total | Average | % Improvement |
|---|---|---|---|---|---|---|---|---|
| | | 1 | 2 | 3 | 4 | | | |
| Control | — | 6.98 | 6.28 | 7.03 | 6.24 | 26.53 | 6.63 | — |
| 2-(2-bromo-4-methylphenylimino)-1,3-dithietane | 20 | 6.39 | 5.73 | 5.85 | 5.86 | 23.83 | 5.96 | 10.0 |
| 2-(2-bromo-4-methylphenylimino)-1,3-dithietane | 60 | 5.99 | 5.39 | 6.32 | 6.23 | 23.93 | 5.98 | 9.8 |

TABLE VI

| Treatment | Level (ppm) | Average Six-Week Lamb Gain (kg) Replication | | | | Total | Average | % Improvement |
|---|---|---|---|---|---|---|---|---|
| | | 1 | 2 | 3 | 4 | | | |
| Control | — | 9.65 | 10.07 | .53 | 8.53 | 9.44 | — | |
| 2-(2-bromo-4-methyl-phenylimino)-1,3-dithietane | 20 | 10.40 | 10.93 | .33 | 10.87 | 43.53 | 10.88 | 15.3 |
| 2-(2-bromo-4-methyl-phenylimino)-1,3-dithietane | 60 | 11.40 | 12.02 | ..17 | 8.37 | 41.96 | 10.49 | 11.1 |

We claim:
1. A compound having the structure:

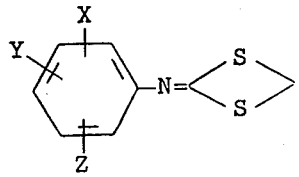

wherein the substituents X, Y and Z are selected from the groups consisting of 2-$CH_3$, 4-Cl; 2-$CH_3$, 4-Br; 2-$CH_3$; 2,5-$(CH_3)_2$; 2,4,5-$(CH_3)_3$; 2-$CH_3$, 3-Cl; 2,4-$(CH_3)_2$; 2,4-$Cl_2$; 2-$OCH_3$; 2-Cl; 2,6-$(C_2H_5)_2$; 2-Cl, 4-$CH_3$; and 2-Br, 4-$CH_3$.

2. A compound according to claim 1 where said groups consist of 2-$CH_3$, 4-Cl; 2-$CH_3$, 4-Br; 2-$CH_3$; 2,5-$(CH_3)_2$; 2,4,5-$(CH_3)_3$; 2-$CH_3$, 3-Cl; and 2,4-$(CH_3)_2$.

3. The compound 2-p-chloro-o-methylphenylimino-1,3-dithietane.

4. A compound according to claim 1 where said groups consist of 4-Cl, 2-$CH_3$; 2-Cl, 4-$CH_3$; 2-Br, 4-$CH_3$ and 2,4,5-$(CH_3)_3$.

5. The compound 2-o-bromo-p-methylphenylimino-1,3-dithietane.

* * * * *